United States Patent [19]

Berlin

[11] Patent Number: 4,911,657
[45] Date of Patent: Mar. 27, 1990

[54] TETHERED BIOMEDICAL ELECTRODE CONNECTOR

[75] Inventor: Lee M. Berlin, Minnetonka, Minn.

[73] Assignee: Lec Tec Corporation, Minnetonka, Minn.

[21] Appl. No.: 325,927

[22] Filed: Mar. 20, 1989

[51] Int. Cl.$^4$ .......................................... H01R 11/00
[52] U.S. Cl. ..................... 439/502; 128/640;
128/798; 439/729; 439/909; 439/258; 439/346; 439/889
[58] Field of Search ............... 439/142, 166, 258, 346,
439/371, 451, 502, 506, 729, 859, 868, 883, 889,
909; 128/639–641, 798

[56] References Cited

U.S. PATENT DOCUMENTS

| | | | |
|---|---|---|---|
| 2,943,627 | 7/1960 | Howell | 128/416 |
| 3,720,209 | 3/1973 | Boldue | 128/2.06 E |
| 3,911,906 | 10/1975 | Reinhold, Jr. | 128/2.06 E |
| 4,072,388 | 2/1978 | Dunn | 128/641 |
| 4,112,941 | 9/1978 | Larimore | 128/2.06 E |
| 4,126,126 | 11/1978 | Bare et al. | 439/909 |
| 4,239,046 | 12/1980 | Ong | 128/640 |
| 4,273,135 | 6/1981 | Larimore | 128/640 |
| 4,671,591 | 6/1987 | Archer | 439/346 |
| 4,674,512 | 6/1987 | Rolfe | 128/640 |
| 4,685,467 | 8/1987 | Cartnell et al. | 128/640 |
| 4,702,256 | 10/1987 | Robinson et al. | 439/729 |
| 4,731,032 | 3/1988 | Noorily | 439/142 |
| 4,797,125 | 1/1989 | Malana | 439/729 |
| 4,798,208 | 1/1989 | Foasse, Jr. | 128/640 |

FOREIGN PATENT DOCUMENTS 675494 12/1963 Canada .

*Primary Examiner*—P. Austin Bradley
*Attorney, Agent, or Firm*—James V. Harmon

[57] ABSTRACT

The present invention provides a lead wire for a medical electrode. The lead wire has a female snap connector at one end. Adjacent to the female snap connector is a male snap connector which is secured to the lead wire by means of a tether. The tether is preferably removably mounted on the lead wire and is most preferably adapted to slide along its length. The male snap connector is moved into proximity of the female connector. The male and female snap connectors are then aligned on opposite sides of a tab portion of a tab-type electrode and are then brought into contact and connected together through the tab to establish both a mechanical and an electrical connection with the tab of the electrode.

12 Claims, 2 Drawing Sheets

TETHERED BIOMEDICAL ELECTRODE CONNECTOR

FIELD OF THE INVENTION

The present invention relates to biomedical devices and more particularly to snap connectors for flexible biomedical electrodes of the kind that are attached to the body for monitoring or stimulation purposes.

BACKGROUND OF THE INVENTION

Two types of biomedical electrodes are used primarily in hospitals for EKG work. Both include a conductive backing laminated to a flexible electrically conductive gel matrix that is applied to the skin of a patient. In one type, a male snap connector is fastened to the backing. During use, a female snap connector at one end of a lead wire is snapped onto the male connector to make electrical contact with the electrode. The other type of electrode has no snap connector and is therefore substantially less expensive. Instead, it has a lateral extension or tab on one side or at the center to which an alligator clip can be fastened as described in U.S. Pat. Nos. 4,674,512 and 4,798,208. The problem with the second type, which will be referred to for convenience as a "tab" electrode, is that it cannot be readily connected to a female snap connector of the type in widespread use for making contact with the snap-type electrodes. As a result, any hospitals and clinics cannot benefit from the cost savings provided by the tab electrodes. Moreover, alligator clip connectors sometimes slip off and are therefore not entirely satisfactory under certain circumstances.

In view of these and other deficiencies of the prior art, it is a general objective of the invention to provide an improved means for using a female snap connector to make electrical contact with a tab electrode that has no male counterpart to the female snap connector, i.e. no male stud. Another object is to enable a lead wire provided with the female snap connector to be used with tab-type electrodes. A further object is to provide a means that allows existing snap-type leads to be reliably connected to a tab electrode or, on other occasions, to be connected in the usual way to a snap-type electrode so that it is not necessary to change leads when making a change from a snap electrode to a tab electrode.

These and other more detailed and specific objectives of the invention will be better understood by reference to the following detailed description and figures which illustrate by way of example but a few of the various forms of the invention within the scope of the appended claims.

SUMMARY OF THE INVENTION

The present invention provides connector means for a biomedical electrode having a lead wire with a female snap connector at one end thereof. Adjacent to the female snap connector is a male snap connector which is secured to the lead wire by means of a flexible tether. The tether is preferably removably mounted on the lead wire and is most preferably adapted to slide along its length. The male snap connector can b moved into proximity of the female connector and aligned with it. The male and female snap connectors are aligned with each other on opposite sides of the tab portion of a tab-type electrode and are then brought into contact and connected to each other through the tab to establish both a mechanical nd an electrical connection with the tab of the electrode.

THE FIGURES

DETAILED DESCRIPTION OF THE INVENTION

Figure 1:
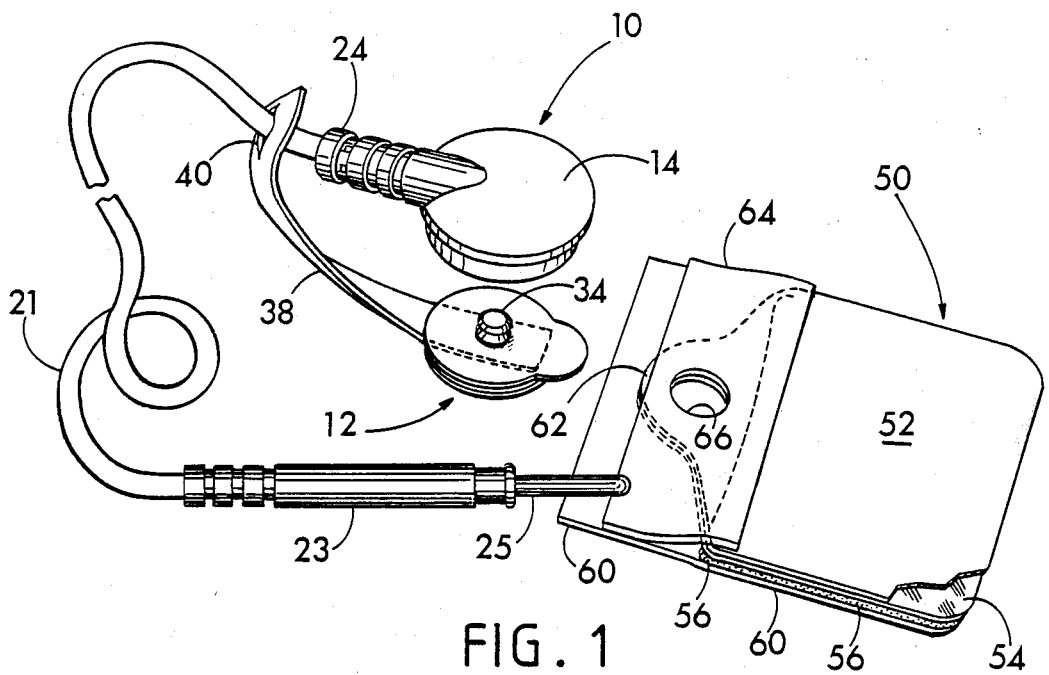
FIG. 1 is a perspective view of the invention just before being attached to a tab type electrode.
Figure 2:
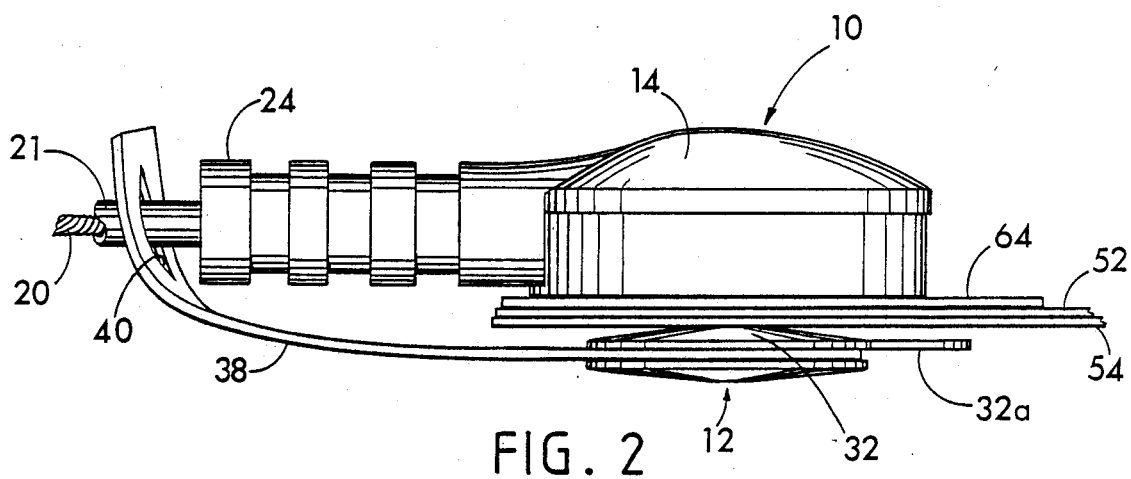
FIG. 2 is a side elevational view of the connector assembly of FIG. 1 on a larger scale after a connection with the electrode has been made.

Shown in the figures is a female snap connector 10 to be used in conjunction with a tethered male snap connector 12 in accordance with the present invention. The female snap connector 10 includes an electrically nonconductive casing 14, e.g. a plastic sheath, within which is a metal connector body 16 having recess or female receptacle 18 that opens downwardly as seen in the figures. Connected to the body 16 is a conductor 20 having an insulated covering 21. At the other end of conductor 20 is a plug 23 with a plug pin 25 which during use is inserted into monitoring or stimulation equipment (not shown).

Casing 14 includes an extension 24 that surrounds the insulated conductor 20 where it enters the female snap connector 10. The connector body 16 is typically hollow and is formed from cup-shaped sheet metal components, the upper one of which is press-fitted at 26 around a lower component 19 that contains the female receptacle 18 at its center. To hold the male snap connector 12 in place, the receptacle 18 can be provided with a spring such as a hairpin spring 28 for that purpose.

The snap connector 12 in accordance with the invention includes an upper stud portion 34 and a lower eyelet portion 30. The eyelet portion 30 includes a central pin 36 which projects axially through the center of the stud 34 for holding the connector 12 together by friction. It will be seen that the stud 34 includes a horizontal stud plate 32 with an extension or tongue 32a which serves as a lifting device for removing the male snap connector 12 from the female snap connector 10 by finger pressure.

In accordance with the invention, a flexible tether 38 is connected to the male snap connector 12. Flexible tether 38 can be formed from a suitable flexible material such as leather, plastic, rubber and the like, plastic sheet material being preferred. Thus, the tether 38 is mounted by placing its right end over the pin 36. The stud 34 and stud plate 32 are then forced downwardly over the pin, securely locking the right end of the tether 38 in place between the stud plate 32 and the pin plate 30. At the left end of the tether 38 is an opening 40 through which the insulated conductor 20, i.e. lead wire, extends. In this way, the tethered snap connector 12 is removably mounted on the lead wire and is preferably slidable thereon. The tether 38 can be easily mounted on an existing female snap connector 10 and its lead wire 20, or removed and replaced whenever required. Usually, once the tether 38 is mounted on a lead wire it is kept there indefinitely, but when not needed for use with a tab electrode, it can be slid back on the wire where it will be out of the way.

Figure 3:
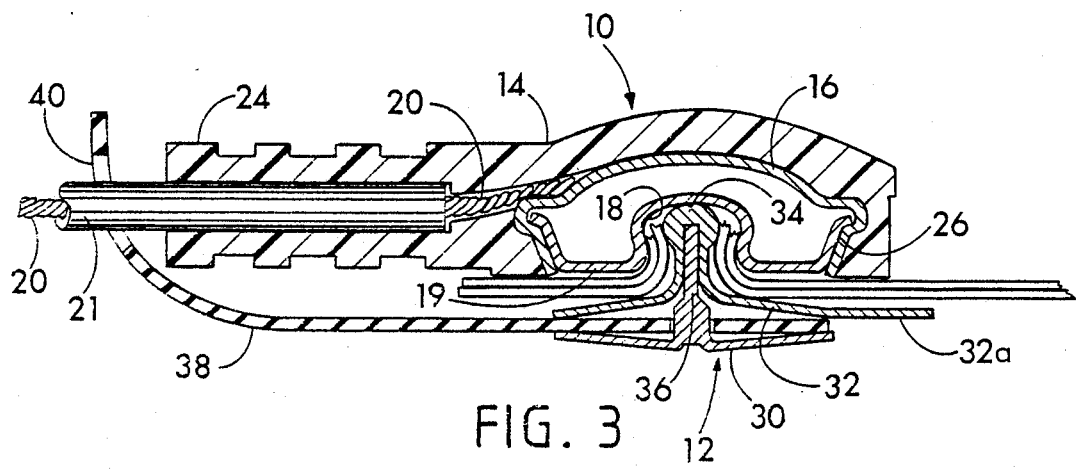
FIG. 3 is a vertical sectional view of FIG. 2.
Figure 4:
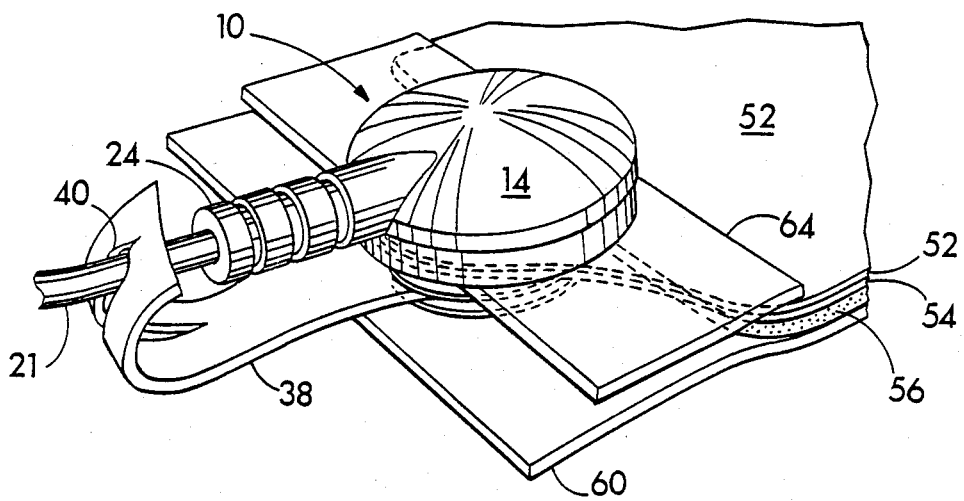
FIG. 4 is a perspective view of he connector assembly in place on an electrode.
Figure 5:
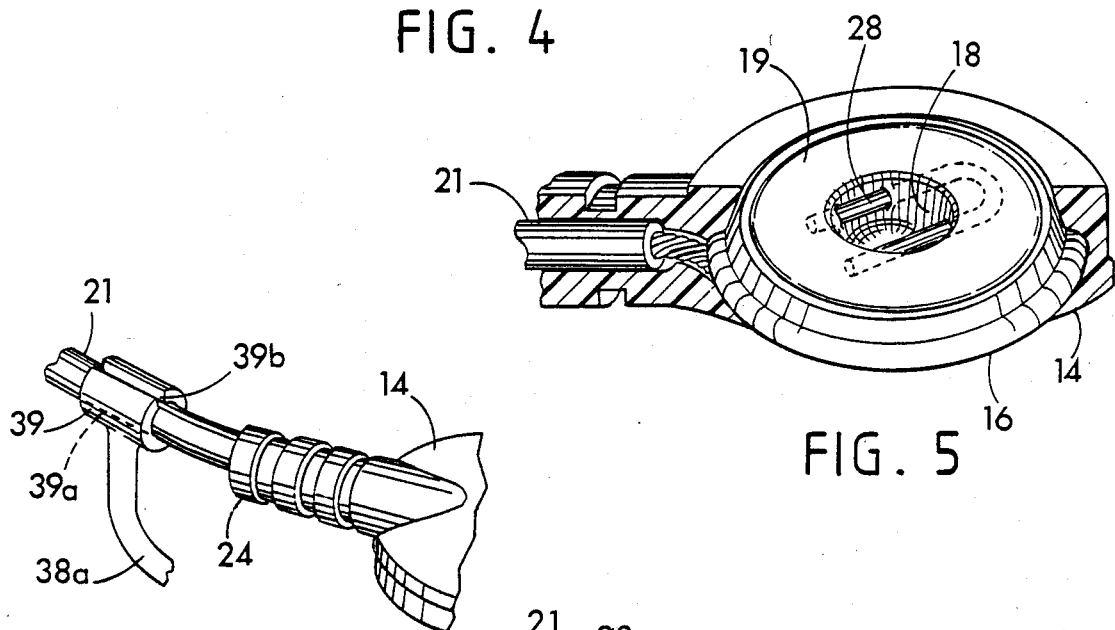
FIG. 5 is a bottom view of the female portion of the connector partly in section.

Also shown in the figures is a flexible biomedical electrode 50 which includes a flexible backing composed of two flexible sheets including an upper electrically insulating sheet 52, e.g. a thin sheet of vinyl plastic, and an electrically conductive layer 54, e.g. a layer of tin or aluminum foil. To the lower surface of conductive layer 54 is laminated a flexible layer of an electrically conductive gel matrix 6 which during use makes electrical contact with the skin of the patient. The matrix 56, which is usually sticky, is covered prior to use with a removable cover sheet 60. Extending to the left, as seen in the figures, is a tab 62 composed of the layers 52 and 54. If desired, there can be applied over the left end portion of the electrode 50 an optional reinforcing tape 64 which in large part covers the tab 62. The reinforcing tape can be used to help support and strengthen the tab 62 and to make possible a more secure connection with he snap connector 10, 12. A punched opening 66 can be provided in the center of the tab 62 and tape 64 when present. In this case, the stud 34 of the male snap connector 12 is simply placed through opening 66 prior to being snapped into the female receptacle 18 of the female snap connector 10. However, as shown in FIG. 3, in the event that the tab 62 does not have a punched opening 66 the stud 34, upon being pressed upwardly into the female receptacle 18, will puncture the tab as shown in the figure, thereby forming a secure snap connection.

Figure 6:
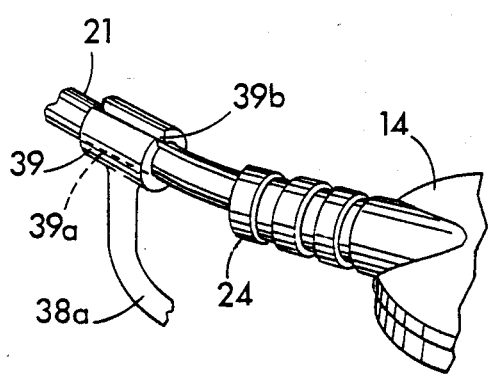
FIG. 6 is a partial perspective view of a modified form of the invention.

Refer now to FIG. 6 which illustrates a modified form of tether in accordance with the invention and wherein the same numerals refer to corresponding parts already described. Shown in FIG. 6 is a flexible tether 38a formed from plastic which in this case rather than being a flat sheet is circular in cross-section. The tether 38a has an enlarged head or collar 39 within which is provided an opening 39a communicating with a slot 39b. To mount the collar 39 over the lead wire 20, the slot 39b is spread temporarily, allowing the collar 39 to be forced onto the insulated lead wire, whereupon the collar will spring back into position as shown in the figure to hold the tether 38a in place.

Figure 7:
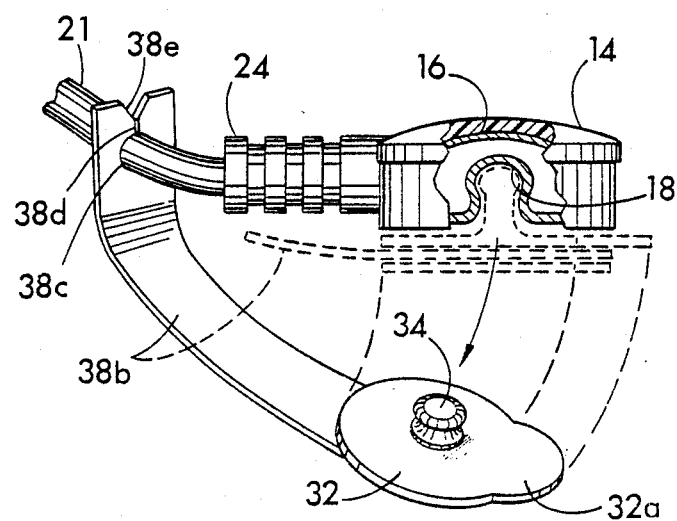
FIG. 7 is a partial perspective view of yet another form of the invention.

Refer now to FIG. 7 which illustrates yet still another embodiment of the invention. In this case the tether 38b comprises a flat sheet of flexible plastic material which can have a degree of stiffness. For example, 30 mil polyethylene plastic sheet can be used. At the left end of the tether 38b is an opening 38c adapted to form a sliding fit over the insulation 21 of the lead wire 20. The opening 38c of the tether 38b has connected to it a slot 38d which is widened at its outer end 38e to make it easier to force the lead wire into the opening 38c. The tether in both FIGS. 6 and 7 can be removed by forcefully pulling it off or, if desired, by sliding it the entire length of the lead wire.

The invention is convenient to use and enables a conventional female snap connector to be connected to both snap-type and snapless tab electrodes. It provides a more secure connection than an alligator clip to a tab type electrode and enables the less expensive tab type electrodes to be used in a variety of circumstances where heretofore only the snap type electrodes could be used. Moreover, the present invention allows greater flexibility in the sense that either snap type or tab electrodes can be used with the same kind of lead wire. The invention is simple in design, rugged in construction and more reliable in operation. Unlike an alligator clip, a snap connector when secured to a tab electrode of the type described cannot be removed by tugging on the lead wire.

Many variations of the present invention within the scope of the appended claims will be apparent to those skilled in the art once the principles described herein are understood.

What is claimed is:

1. A biomedical electrode connector for making electrical connection with a flexible biomedical electrode of the type that is secured during use to the skin of a patient, said connector comprising a lead wire having a female snap connector at one end thereof, a male snap connector sized to fit the female snap connector and a tether connected at one end to the male snap connector and removably connected at the other end to the lead wire, the male snap connector being moveable to a position in alignment with the female snap connector, said male snap connector having a stud that is passed through the tab of the flexible electrode and into contact with female snap connector to form a snap-fit connection in the female snap connector.

2. The connector of claim 1 wherein the male snap connector comprises a stud plate having an upwardly extending stud projecting vertically therefrom and an eyelet with a pin connected to the stud and said tether is secured to the male snap connector between the stud plate and the eyelet.

3. The connector according to claim 1 wherein the tab of the flexible biomedical electrode is pre-punched with a hole to receive a stud provided on said male snap connector.

4. The connector of claim 1 wherein the electrode has a tab with a hole therein to facilitate the connection between said female connector and male connector.

5. The connector of claim 1 wherein the tether is formed from a flexible electrically nonconductive material and one end of the tether is slidably mounted upon the lead wire.

6. The connector of claim 5 wherein the tether has an opening in one end thereof and said opening is slidably mounted upon the lead wire.

7. The connector of claim 1 wherein the male snap connector includes a laterally projecting tongue to assist the male snap connector in being released by the application of finger pressure to the tongue.

8. The connector of claim 7 wherein the male snap connector includes a vertically disposed stud having an enlarged head, a stud plate and an eyelet having a pin frictionally connected to the stud and said tongue comprises a lateral extension of said stud plate.

9. The connector of claim 1 wherein the tether includes an opening adapted to receive the lead wire and a slot through which the lead wire can be forced into said opening and said tether is sufficiently resilient to enable portions thereof adjacent the slot to snap together around the lead wire.

10. The connector of claim 9 wherein the tether includes a collar having an opening therethrough and a slot connected to the opening for introducing the lead wire into the opening within the collar.

11. The connector of claim 9 wherein the tether is formed from flat sheet material, an opening is provided therein adjacent one end of the tether for the lead wire, a slot is provided in the sheet material for introducing the lead wire into the opening, and the slot has an enlarged entrance to assist in the introduction of the lead wire into the opening of the tether.

12. A biomedical electrode connector for making electrical connection with a flexible biomedical electrode of the type that is secured during use to the skin of a patient, said connector comprising a lead wire having a first snap connector at one end thereof, a second snap connector sized to fit the first snap connector and a tether connected at one end to the second snap connector and connected at the other end to the lead wire, one of the snap connectors comprising a male snap connector and the other comprising a female snap connector, the male snap connector being moveable to a position in alignment with the female shape connector, said male snap connector having a stud that is passed through the tab of the flexible electrode and into contact with female snap connector to form a snap-fit connection in the female snap connector.

* * * * *